United States Patent [19]
Relman et al.

[11] Patent Number: 6,036,960
[45] Date of Patent: Mar. 14, 2000

[54] **FILAMENTOUS HEMAGGLUTININ OF *B. PERTUSSIS***

[76] Inventors: David A. Relman, 785 Roble, No. 5, Menlo Park, Calif. 94025; Mario Domenighini, via Fiorentina 1, 53100 Siena; Rino Rappuoli, via Calamandrei 37, Quercegrossa, 53100 Siena, both of Italy; Stanley Falkow, 8 Longspur, Portola Valley, Calif. 94025

[21] Appl. No.: 08/299,941

[22] Filed: Sep. 1, 1994

Related U.S. Application Data

[63] Continuation of application No. 07/928,619, Aug. 10, 1992, abandoned, which is a continuation of application No. 07/436,297, Nov. 13, 1989, abandoned, which is a continuation-in-part of application No. 07/263,648, Oct. 27, 1988, abandoned.

[51] Int. Cl.⁷ ........................... A61K 39/10; G01N 33/53; C12P 21/06; C12P 19/34
[52] U.S. Cl. ..................................... 424/253.1; 424/253.1; 435/7.1; 435/69.1; 435/69.3; 435/91.1; 435/252.3; 435/253.1; 435/320; 435/325.1; 536/22.1; 536/23.1; 536/23.7; 536/24.32; 536/124.32
[58] Field of Search ................................... 536/22.1, 23.1, 536/23.7, 24.32; 435/69.1, 69.3, 71.1, 320.1, 252.3, 325.1, 91.1; 424/253.1

[56] References Cited

U.S. PATENT DOCUMENTS 5,211,657  5/1993  Yamada et al. .............................. 623/1

OTHER PUBLICATIONS

Charles et al PNAS 86: 3554–3558,1989.
Fidel Dissertation Abstracts 1988, vol. 49/12–B p. 5110.
Evans et al FEBS Letters 208:211–216, 1986.
Reisner et al Develop. Biol. Standard 61:265 271, 1985.
Stibitz et al Zbl. Bakt. Suppl. 17: 195–200, 1988.
Relmann et al Proceeding of the Nat Acad of Sci. 86:2637–2641, 1989
Stibitz et al, J. Bact. 170:2904–2913, 1988.
Mattei et al FEMS Lett 37: 73–78, 1986.
Brown et al Infect & Immunity 55: 154–161, 1987.
Houghten et al, Vaccine 86, pp. 21–25.
Dellisse–Galthorpe et al, Infection & Immunity 82: 2895–2905.
Bowie, J.V. et al. Science 247: 1306–1310 (1990).
Kumar, V. et al. Proc. Natl. Acad. Sci. USA 87: 1337–1341 (1990).
Itakura et al Science vol. 209 pp. 1401–1405 (1980).
Maniatis et al Molecular Cloning A Laboratory Manual pp. 403–433 (1982).
Smith et al, Nature vol. 321 pp. 674–679 (1986).
Henikoff, et al Gene vol. 8 pp. 351–359 (1984).
Steinert et al Nature vol. 302 pp. 794–800 (1983).
Stibitz et al, Journal of Bact. vol. 170 p. 2904–2913 (1988).
Brown et al Infect Immun vol. 55 p 154–161 (1987).
Maniatis et al, Molecular Cloning, A Laboratory Manual, Cold Spring Habor Laboratory, CSH, NY (1983) p270–307.
Brown and Parker, "Cloning of the Filamentous Hemagglutinin of *Bordetella pertussis* and its Expression in *Escherichia coli*" *Infection and Immunity* (1987) 55(1):154–161.
D. Mattei et al., "Molecular Cloning of a Coding Sequence of *Bordetella pertussis* Filamentous Hemagglutinin Gene", *FEMS Microbiology Letters* (1986) 37:73–77.
S. Stibitz et al., "Genetic Analysis of a Region of the *Bordetella pertussis* Chromosome Encoding Filamentous Hemagglutinin and the Pleiotropic Regulatory Locus vir", *J.of Bacteriology* (1988) 170(7):2904–2913.
Y. Sato et al., "Separation and Purification of the Hemagglutinins from *Bordetella pertussis*", *Infection and Immunity and Immunity* (1983) 41(1):313–320.
J. Reiser et al., "*Bordetella pertussis* Filamentous Hemagglutinin Gene: Molecular Cloning of a Potential Coding Sequence", *Develop. Biol. Standard* (1984) 61:265–271.

*Primary Examiner*—James C. Housel
*Assistant Examiner*—Ja-Na A. Hines
*Attorney, Agent, or Firm*—Richard F. Trecartin; Flehr Hohcach Test Albritton & Herbert LLP

[57] ABSTRACT

Nucleic acid and protein compositions are provided from *B. pertussis* which may find use in diagnosis, prevention and therapy of whooping cough. Particularly, an open reading frame encoding filamentous hemagglutinin precursors provided, with the intact protein for the filamentous hemagglutinin portion thereof, can be expressed in a wide variety of hosts, for use in the production of antibodies, for immunodiagnosis or therapy, or as vaccines for prophylactic purposes.

24 Claims, No Drawings

FILAMENTOUS HEMAGGLUTININ OF B. PERTUSSIS

CROSS REFERENCE TO RELATED APPLICATIONS

This is a continuation of application Ser. No. 07/928,619 filed Aug. 10, 1992, which is a continuation of Ser. No. 07/436,297, filed Nov. 13, 1989, now abandoned, which is a continuation-in-part of application Ser. No. 263,648, filed Oct. 27, 1988, now abandoned, which is incorporated herein by reference.

INTRODUCTION

1. Technical Field

This invention relates to the gene encoding filamentous hemagglutinin of B. pertussis, the protein product and the use of the gene and the product for developing vaccines by genetic engineering techniques.

2. Background

Bordetella pertussis is a small gram negative bacillus found only in humans. It is the etiologic agent of the childhood disease whooping cough, also known as pertussis. In susceptible individuals, the disease may progress to a serious paroxysmal phase. Violent and spasmodic coughing occurs, with the patient being subject to secondary injury from the hypoxia and convulsions attendant with the coughing paroxysms. Secondary infections, encephalopathy and death may occur. The discrete molecular moiety that has been associated with the severe effects in the paroxysmal stage of the disease is pertussis toxin (PTX). PTX has been reported under a variety of names, including lymphocytosis promoting factor, histamine sensitizing factor and islet-activating protein.

Another protein, filamentous hemagglutinin (FHA) is a surface associated protein expressed by B. pertussis under the control of a trans-acting vir locus. FHA, while poorly characterized, is thought to act as a major adhesion and immunodominant antigen in the course of human infection. This protein appears as a heterogeneous collection of polypeptide species on sodium dodecylsulfate-polyacrylamide gel electrophoreses, ranging from approximately 60 to 220 kDa (kilodaltons). It is likely that most of the smaller, commonly seen protein gel bands represent degradation products of a dominant 220 kDa species. Electron microscopy of this protein reveals a filamentous structure with dimensions of 2 nm by 40–100 nm.

It has been suggested that FHA is one of the most important factors mediating the bacterial-eukaryotic cell adhesive interactions. Furthermore, FHA stimulates an immune response in humans following clinical disease and acts as an immunoprotective antigen in a model system employing aerosol challenge of immunized mice. Although less effective than PTX when used alone, FEA and PTX together demonstrate a synergistic immunoprotective effect.

RELEVANT LITERATURE

A description of the B. pertussis hemagglutinin protein may be found in Irons et al., J. Gen. Microbiol. (1983) 129:2769–2778; Arai and Sato, Biochem. Biophys. Acta (1976) 444:765–782; and Zhang et al., Infect. Immun. (1985) 48:422–427. Physiological properties are described by Tuomanen and Weiss, J. Infect. Dis. (1985) 152: 118–125; Lenin et al., FEMS Microbiol. Lett. (1986) 37:89–94; Urisu et al., Infect. Immun. (1986) 52:695–701; Redd et al., J. Clin. Microbiol. (1988) 26:1373–1377; Oda et al., J. Infect. Dis. (1984) 150:823–833; Robinson and Irons, Infect. Immun. (1983) 40:523–528; Sato and Sato, ibid. (1984) 46:415–421; and Ad Hoc Group for the Study of Pertussis Vaccines, Lancet i (1988) 955–960.

Cloning of the filamentous hemagglutinin structural gene or fragment thereof has been reported by Brown and Parker, Infect. Immun. (1987) 55:154–161; Reiser et al., Dev. Biol. Stand. (1985) 61:265–271; Mattei et al, FEMS Microbiol. Lett. (1986) 36:73–77 and Stibitz et al., J. Bacteriol. (1988) 170:2904–2913.

Chemical analysis of the filamentous hemagglutinin has been reported by Sato et al., Infect. Immun. (1983) 41:313–320.

SUMMARY OF THE INVENTION

DNA sequences encoding at least a portion of the B. pertussis fhaB gene, genetically engineered products including such sequences, the expression products of such sequences, and cells containing such genetically engineered sequences are provided for use in the diagnosis, prophylaxis and therapy of whooping cough.

DESCRIPTION OF THE SPECIFIC EMBODIMENTS

The subject invention concerns nucleotide sequences associated with the filamentous hemagglutinin protein of B. pertussis and their use in the diagnosis prophylaxis and therapy of whooping cough or pertussis. The open reading frame is about 10 kbp (specifically about 10789 bp) as the sequence set forth in the experimental section. It encodes a protein of about 368 kDa (about 3597 amino acids), comprising an N-proximal fragment of 230 kDa, which N-proximal fragment is divided by proteolysis into two polypeptide fragments of about 98 and 140 kDa at an arginine-rich peptide sequence RRARR, which are the N-terminal and C-terminal fragments, respectively. This sequence may act as a proteolytic cleavage site. The overall polypeptide is basic, has a relatively high charge density, a $pK_I$ of 9.65 and a net charge of +19. Alanine and glycine constitute 27% of the total residues, while only 3 upstreams are present. The last 350 amino acids provide a highly basic region (charge +32; $pK_I$ 11.3) rich in proline (17%). At amino acid position 1097 (defined by the start of translation at 253 bp from the left-hand EcoRI site) and again at position 2599 is the tripeptide sequence RGD. This sequence is known as a "cell recognition site" for the interaction of fibronectin and other eukaryotic extracellular matrix proteins with certain eukaryotic cell receptors, particularly mammals, and may function in a similar manner in FEA mediated bacterial adherence.

Previously, the inventors identified an open reading frame of about 10 kbp encoding a protein of about 313 kDa, which is divided into two polypeptide fragments of about 99 and 214 kDa by an arginine-rich peptide sequence RRARR. Computer analysis identified an open reading frame (ORF) 9375 bp long beginning at the ATG translational start codon 253 bp from the left-handed EcoRI site. The ORF and preferred codon usage end at a TGA stop codon 9625 bp from the left-hand EcoRI site. The predicted amino acid sequence of the FHA ORF was 3125 residues long, with a calculated molecular weight of 313 kd.

The gene appears to be located adjacent to the vir locus. In the direction defined by transcription an apparent regulatory gene fhaA lies about 2–5 kb downstream from fhaB, followed by the gene fhaC, also believed to be a regulatory gene, again in the downstream direction from fhaA. The beginning of the ORF is separated by approximately 430 bp from the first of the bvg genes bvgA. The gene begins at position 253 from the left at the pDR$_1$ EcoRI site and ends at position 11040 with a TAG codon.

The fhaB gene is characterized by having a high GC content, namely about 67.5%. In addition, there is a series of tandem direct nucleotide repeats of the pattern ABABA in the region from nucleotide 1468 to nucleotide 1746, with the G of the sequence reported in the Experimental section being nucleotide 1. An unusual alternating repeat (PK)$_5$ begins at residue 3477. The sequence VEVVPRKVET at position 3319 is repeated at position 3360. Transcriptional initiation appears to occur 70–75 bp upstream of the ORF.

Fragments of the open reading frame of at east about 15 bp, more usually at least about 50 bp, and usually at least about 100 bp may find use in a variety of ways. The fragments may be used for diagnostic purposes, as probes in hybridizing to DNA or RNA for detecting the presence of *B. pertussis* or the like. Use of Southerns, Northerns, dot-blot, or other techniques may be employed. The fragments may be used for encoding peptides of at least about 9 amino acids (27 bp) usually at least about 12 amino acids.

The fragments may also be used in the antisense direction to modulate the amount of the expression product of the fhaB gene, where such modulation may be of interest. Thus, the infectious ability of the organism may be modulated and/or attenuated by reducing the presence of the filamentous hemagglutinin protein on the surface of the organism.

Fragments of interest of the fhaB gene include those fragments associated with the expression of the 98 kDa protein and the 230 kDa protein. Using the numbering as set forth in the sequence provided in this application, the fragment for the 98 kDa protein would terminate between nucleotides 3402 and 3502, usually between 3451 and 3474. The 230 kDa protein is initiated in that region and terminates at about nucleotide 9624. When FHA is originally isolated and purified from *B. pertussis* liquid culture supernatant using standard techniques there are often 3–4 bands seen on SDS-PAGER with polypeptide species of 230, 140, 125 and 98 kDa. With increasing time of storage, two new species appear, 75 and 58 kDa with concurrent fading of the 230 kDa band and intensification of the 125 and 98 kDa bands. An identical N-terminal sequence is observed for the 140 and 125 kDa fragments: A-L-R-Q-D-F-F-T-P-G-S-V-V-V-R-A-Q-G-N. This peptide is encoded begining at position 1074, immediately downstream from a proposed proteolytic cleavage site R-R-A-R-R, and terminating at position 1131. Also of interest is the repeat sequence, where the sequence should have at least two repeats, preferably three repeats, and the fragment will be at least about 60 nucleotides, more usually about 100 nucleotides, and may be 278 nucleotides or more, usually not exceeding about 300 nucleotides of the open reading frame, the latter encompassing the entire repeat region. The repeats do not have perfect homology, but show a high degree of conservation.

Regions of interest will be those encoding amino acid sequences 1211 to 1216 (E-A-R-K-D-E), 1876 to 1881 (R-K-D-E-H-R) and 3075 to 3080 (S-K-Q-D-E-R), and adjoining amino acid sequences, extending up to 100 amino acids, usually up to 50 amino acids in either direction, but particularly including at least 3 amino acids of the sequences described above. DNA sequences of interest may include fragments of 3490 to 3590, 3840 to 3940, 5840 to 5940, 9440 to 9540, and fragments of at least 15 bp, more usually at least 25 bp thereof. The fragment from about 5625 to 5780 does not appear to have any features of interest and may be excluded, unless joined to one of the fragments indicated above.

Antisera prepared against the *B. pertussis* FHA protein cross-reacts with polypeptide species of *B. parapertussis* and *B. bronchiseptica.* Antisera binding to the expression products of the regions 2836–3786 nt, 5212–7294 nt and 6393–8080 nt bound to peptides of *parapertussis,* while only the antisera of the first two bound to peptides of *brochiseptica.*

The subject protein or any portion thereof may be prepared in any convenient host, preferably prokaryotic. By transforming an appropriate host with the expression construct, the host will express the polypeptide of interest, which may then be isolated or, as appropriate, the host may be isolated containing the subject protein or portion thereof and used as a vaccine.

The expression construct or cassette will employ a transcription initiation region, the structural gene for the polypeptide to be expressed, and and a transcriptional termination region. The transcriptional initiation region may include only the RNA polymerase binding site or may also include an enhancer or operator to provide for increased expression of the subject protein or portion thereof, or inducible expression of the subject protein or portion thereof.

A large number of transcription initiation regions are known which are active in one or more prokaryotic hosts, such as the lambda left or right promoters, the lac promoter, the trp promoter, the tac promoter, omp promoter, metallothionein promoter, etc. The natural promoter may also find use. The particular promoter will be chosen to provide for efficient expression in accordance with the selection of the host cell line.

For the most part, prokaryotic host cell lines will be used to provide for efficient expression of the filamentous hemagglutinin or portion thereof, integrity of the expression product, ease of isolation of the expression product, and in some situations, the ability to use the host without isolation of the protein, using the transformed host as the vaccine. Various organisms may be used which may provide for an immune response not only to the subject proteins or portions thereof, but also to other pathogens, so that the vaccine will result in immune protection, not only against the *B. pertussis* organism but also against disease caused by other pathogens.

Various host organisms which may be used include various gram negative organisms, such as *E. coli,* Salmonella, Yersinia, Pseudomonas, Bordetella, such as the species *avium, bronchiseptica, parapertussis* and *pertussis,* where the last two are particularly preferred.

A previously indicated sequence analysis of the subject protein indicates a guanine plus cytosine content considerably higher than that of the traditional *E.coli* cloning host (approximately 50%). Therefore, for the most part, the host will desirably have a high guanine plus cytosine content in its genome, preferably at least 60%, more preferably 65%. However, one may use synthetic portions to reduce the ratio of guanine and cytosine for use in organisms lacking a preference for GC.

Various replication systems are available for use in the various host species. For the most part, the vectors will include not only a functional replication system but a marker for selecting transformants comprising the subject structural gene or portion thereof. While it is usually desirable to employ either a plasmid or virus which is stably maintained as a vector without lysogeny, to enhance the efficiency of expression by having a multicopy replication system which is stable in the host, this is not necessary. Thus, one can transform with bare DNA comprising the expression cassette in combination with a marker for selection, where the marker may be joined to the expression cassette or be independently present in the transformation media. In some situations, a vector will be employed which does not have a stable replication system for the expression host. In this manner, selection can be carried out to insure that integration has occurred by selecting for those cells containing the marker.

A wide variety of markers may be used which include antibiotic resistance, resistance to heavy metals, imparting prototrophy to an auxotrophic host, or the like. The particular choice of marker is not critical to this invention, but will be selected for efficiency in selection and efficiency in production of the subject protein or portion thereof.

Depending on the manner of transformation, as well as the host, various other functional capabilities may be provided in the vector. For example, transfer capability may be provided which allows for conjugation in conjunction with a helper plasmid, where once transferred to the recipient host, the vector may no longer be transferred to other hosts. For example, the rlx sequence may be employed, particularly from the P-1 incompatibility group. In addition, the cos site may be employed from bacteriophage lambda. Other markers of interest may include a gene which renders an antibiotic resistant strain sensitive.

The termination region is not critical to this invention and any convenient termination region may be used. The native termination region may be employed or a termination region which is normally associated with the transcription initiation region or a different region. The fact is that many transcription termination regions have been employed and are generally available and may be used with advantage.

The host may be transformed in any convenient way. By using bare DNA, calcium phosphate precipitated DNA may be employed for transformation. Alternatively, conjugation may be employed using a helper plasmid, where a transfer gene is provided in a vector. In some instances, it may be desirable to employ a bacteriophage vector, where the host cell will be transduced or transfected. The technique for introducing the expression cassette comprising the subject gene or portion thereof is not critical to this invention and various alternative protocols find ample exemplification in the literature.

The subject gene may also be subject to various lesions or mutations. For example, the sequence RRARR may be substituted, deleted, or modified so as to remove the peptidase cleavage site. Thus, the protein would be retained substantially intact, with the two potential fragments fused together. This protein could find a variety of uses. Other mutations may include the removal of the upstream portion of the gene, so as to leave only the sequence that is downstream from the RRARR sequence, where an initiation codon may be introduced at the appropriate site. In addition, mutagenesis of an RGD region may cause altered interactions with eukaryotic target cells and perhaps an altered host immune response, both of which may prove useful for disease therapy or prophylaxis.

Mutation can be achieved in a variety of ways using in vitro mutagenesis, primer repair, the polymerase chain reaction, restriction site deletions, insertions, or the like. The particular manner in which the subject gene is modified is not critical to this invention and any conventional technique may be employed which provides for the desired substitutions, deletions or insertions.

The subject gene can be obtained by EcoRI digestion of the plasmid pUW21–26. The resulting 10 kb EcoRI fragment contains the open reading frame of 9375 bp. This fragment may be manipulated at its 5' terminus in a variety of ways. By employing Bal 31 digestion, the sequence may be resected to remove all or a portion of the non-coding region 5' of the initiation codon. Alternatively, one may restrict either upstream or downstream from the initiation codon, where the nucleotides removed by restriction downstream from the initiation codon may be replaced with an appropriate adapter. In this manner, the subject sequence may be inserted into a polylinker downstream from a transcriptional initiation regulatory region and be under the transcriptional initiation regulation of such region.

The subject compositions, both nucleotides and proteins, may find both diagnostic and therapeutic use. For diagnostic use, as already indicated, the sequences may be used to detect the presence of nucleic acid sequences which duplex with the subject sequences as indicative of the presence of *B. pertussis.* Alternatively, the protein or portion thereof may be used in diagnostic assays, as a labeled or unlabeled reagent for detection of antibodies to the filamentous hemagglutinin in a blood sample or the presence of filamentous hemagglutinin protein in a blood or tissue sample.

Intact protein or portion thereof may be used to prepare antibodies which may be used in diagnosis, prophylaxis or therapy. The antibodies may be polyclonal or monoclonal, preferably monoclonal. Desirably, neutralizing antibodies will be obtained. Antibodies may be mouse antibodies, human antibodies, chimeric antibodies, e.g., mouse variable region and the human constant region, or the like. Of particular interest are those constant regions which bind to complement, such as IgM and IgG isotypes. The antibodies may be used for passive immunization or for treatment in accordance with conventional ways.

The subject compositions also find use as vaccines, as the protein, by itself or in combination with other proteins, e.g., acellular compositions, as cellular compositions in a pertussis or non-pertussis host, in purified or semi-purified form or the like. Desirably, the subject compositions are used in conjunction with a modified pertussis toxin, where the toxin no longer has ADP-ribosyltransferase activity, particularly subunit A. This can be achieved by using ptx3201 as described in Black et al., *Science* (1980) 240:656–659. By introducing the subject gene under the transcriptional initiation regulatory control of a constitutive promoter or an inducible promoter, which is not regulated by the normal pertussis transcriptional regulation of the filamentous hemagglutinin gene, one can provide for the enhanced presence of the subject protein on the surface of the *B. pertussis* cell. In this way, an enhanced immune response may be achieved in response to vaccinating either live or dead organisms.

Because of the various ways in which the subject composition may be administered, the amount administered will vary widely. In addition, the amount of the vaccine will vary in accordance with the nature of the administration, the frequency of the administration, the presence or absence of antigen, the nature of antigen, or the like.

The manner of administration may be oral, peritoneal, subcutaneous, intravascular or the like. Usually, an inert carrier is employed, such as sugar, water, aqueous ethanol, phosphate buffered saline, saline, or the like. Adjuvants include aluminum hydroxide, vegetable oils, bacterial toxins, etc. The amount of the active ingredient will generally be in the range of about 25 to 75 μg/kg for a single human dose. Pertussis vaccines have been used previously, and prior usage may be used as a guide for the dosage employed. See, for example, *Developments in Biological Standardization*, supra.

The following examples are offered by way of illustration and not by way of limitation.

EXPERIMENTAL

Materials and Methods

Bacterial Strains and Plasmids

*B. pertussis* strain BP536 is a spontaneously-occurring streptomycin resistant mutant of the virulent phase (I) parental strain BP338. BP537 is an avirulent phase variant of BP536. The isolation of the Tn5 mutant BP353 has been previously described, Weiss et al., *Infect. Immun.* (1983) 42:33–41; the transposon insertion site has been mapped more recently (Stibitz et al., 1988, supra) BP338 Tn5–25 carries a Tn5 insertion mutation within the 2.4 kb BamHI segment of fhaB (Stibitz et al., 1988, supra). BP-TOX6 (available from R. Rappuoli) is a derivative of BP536 with a deletion of the pertussis toxin operon and the substitution of a kanamycin resistance cassette at that location. BP-B52 (available from F. Mooi) is a BP536 derivative which carries insertion mutations which inactivate the fim2 and fim3 genes independently. *E. coli* strains JM101 and SM10 have been described elsewhere (Messing, *Recomb. DNA Tech. Bull.* (1979) 2:43–48; Simon et al., *Bio/Technology* (1983) 1:784–791). Cosmid pUW21–26 is a derivative of pHC79 (Hahn and Collins, *Gene* (1980) 11:291–298) with an approximately 45 kb insert, containing the cloned vir and fha loci from BP338 (Stibitz, 1988, supra). The construction of plasmid vector pRTP1 has been described (Stibitz et al., *Gene* (1986) 50:133–140).

Cloning of fhaB and Construction of fhaB Deletion Mutants

The filamentous hemagglutinin (FHA) structural gene, fhaB, was cloned on a 10 kb EcoRI fragment from cosmid pUW21–26 into the vector pRTP1, creating the recombinant plasmid pDR1. An in-frame partial deletion of fhaB was constructed by re-ligating a pool of BamHI partial digests of pDR1. Plasmids were screened for the loss of an internal 2.4 kb BamHI fragment. The resultant plasmid was designated pDR101.

Bacterial Conjugations and Allelic Exchange

The technique for conjugal transfer of pRTP1 derivatives from *E. coli* to *B. pertussis* has been described (Stibitz et al., 1986, supra). The partially deleted copy of fhaB was exchanged for the wild type allele in *B. pertussis* BP536 in two steps. First, the *E. coli* donor, SM10(pDR101), was mated with a *B. pertussis* recipient, BP536 Tn5-25, which carries a selectable marker within the fhaB fragment to be deleted. $Sm^R Ap^R$ exconjugants were then plated on media containing Sm alone and screened for the loss of Km resistance, indicating a second crossover event and acquisition of the mutant allele.

DNA Sequencing and Sequence Analysis

The 10 kb EcoRI fragment containing fhaB was subcloned as three separate BamHI fragments as well as random one to three kb Sau3A fragments in M13mp18 and M13mp19 (Yanisch-Perron et al., *Gene* (1985) 33:103–119), pEMBL18 and -19 (Dente et al., *Nucleic Acids Res.* (1983) 11:1645–1655), or Bluescript (Stratagene, San Diego, Calif.) vectors. DNA inserts were sequenced by the dideoxy chain-termination method (Sanger et al., *Proc. Natl. Acad. Sci. USA* (1977) 74:5463–5467), using either Klenow fragment or Sequenase (U.S. Biochemical Corporation, Cleveland, Ohio). Synthetic oligonucleotide primers were designed in order to extend sequence reading across large cloned inserts. Assembly of the nucleotide sequence was performed using the software package of the University of Wisconsin Genetics Computer Group (Madison, Wis.). Further analysis of the completed nucleotide and predicted peptide sequences was performed, using both this package as well as PC/GENE (Intelligenetics, Mountain View, Calif.).

Hemagglutination

The ability of *B. pertussis* strains to agglutinate sheep erythrocytes was assayed in conical pointed-bottom wells of polystyrene Microtiter plates (Dynatech Laboratories, Alexandria, Va.). The strains were grown for two to three days on Bordet-Gengou plates, washed twice in phosphate-buffered saline, and resuspended to an $OD_{600}$ of 10 (1.7× $10^{10}$ cells/ml). The first well of a microtiter plate received 100 μl of this cell suspension, following which the bacteria were two-fold serially diluted 11 times. Sheep erythrocytes were added to each well as 50 μl of a 0.5% PBS-washed suspension. The plates were left at room temperature for three to four hours during which time nonagglutinated erythrocytes slid down the well bottoms forming a dark pellet. Hemagglutinating (HA) activity was expressed as the inverse of the highest dilution without significant pellet formation.

Western Immunoblots

Polyacrylamide gel electrophoresis was performed in the presence of sodium dodecylsulfate with a 10% separating gel and 20 μl of boiled ($OD_{600}$=10) *B. pertussis* cell suspension with sample buffer. Transfer of protein to nitrocellulose membrane followed the procedure of Towbin et al, *Proc. Natl. Acad. Sci. USA* (1979) 76:4350–4354. Nonspecific antibody binding to the membrane was blocked by pre-incubation with a solution of PBS and 1% nonfat dry milk. Immunological detection of FRA was performed using a 1:1000 dilution of a mixture of (1–54, 1–199, 31E2, 22F10, and 68A6) monoclonal anti-FHA antibodies (obtained from F. Mooi), followed by incubation with a 1:250 dilution of horseradish peroxidase-conjugated goat anti-mouse antisera. HRP activity was detected using a tetramethylbenzidine-containing reaction mixture. fim2 and fim3 production were detected using the same technique and monoclonal antibodies (21E7 and 8E5) specific for these two proteins (obtained from F. Mooi).

Southern Hybridization

*B. pertussis* chromosomal DNA was isolated, digested with restriction endonucleases, and separated by agarose gel electrophoresis according to standard techniques (Maniatis et al. (1982), *Molecular Cloning: A Laboratory Manual*, Cold Spring Harbor Laboratory, Cold Spring Harbor, N.Y.). Transfer of fragments to nitrocellulose followed the method of Smith and Summers (*Anal. Biochem.* (1980) 109:123–129). Hybridization with probe occurred at 37° C., with 50% formamide and 5xSSC. Membranes were washed twice with 2xSSC at 25° C., twice with 0.1xSSC at 25° C., and then twice with 0.1xSSC at 65° C.

In vitro Bacterial Adherence

*B. pertussis* strains were grown on plates for two days and then washed twice in phosphate-buffered saline (PBS). 20 μl of bacterial suspension ($OD_{600}$=10) was added to tissue culture plate wells containing 200 µl of MEM and a cover slip on which approximately $5\times10^4$ Chinese Hamster Ovary cells had been innoculated and allowed to grow overnight. After incubation at 37° C., 5% $CO_2$, for four hours, each well was washed vigorously with PBS three times. Any remaining bacteria and CHO cells were fixed with methanol and then stained with Giemsa. All bacterial strains were studied in duplicate and all experiments repeated at least twice. Bacteria adherent to a single CHO cell were counted visually and the mean with standard deviation determined for each strain. Joint 95% confidence intervals were computed based on central limit theorem approximations and Bonferoni techniques.

Results

Identification and Cloning of the FHA Structural Gene

Previous work had led to the isolation of a cosmid clone, pUW21-26, which hybridized with both vir and fha DNA probes (Stibitz, et al., 1988, supra). The analysis of Tn5 insertion mutations within this cosmid, using FRA colony and Western immunoblots, had suggested that the FHA structural gene, fhaB, was located on a 10 kb EcoRI fragment just to the right of the vir locus. Furthermore, fhaB transcription was believed to begin near the left-hand EcoRI site and proceed from left to right, based upon the correlation of FHA truncated product size with location of the corresponding Tn5 insertion site.

Deletion of the internal 2.4 kb BamHI fragment of fhaB was performed as described above and the mutation returned to the B. pertussis chromosome, yielding strain BP101. The structure of the resultant fhaB mutant locus in this strain was confirmed by Southern blot analysis. The largest FHA cross-reactive polypeptide produced by BP101 measures approximately 150 kDa, as determined by Western blot technique. This truncated FHA product has no hemagglutinating activity.

These data confirmed that the structural gene for FHA must be contained on the 10 kb EcoRI insert of pDR1. This fragment was, therefore, subcloned for dideoxy single-stranded DNA sequencing.

Construction of fhaB Fusion Proteins

Seven portions of the fhaB ORF were each cloned into the expression vector pEX34. The result in each case was a translational fusion with the first 98 amino acids of the phage MS2 RNA polymerase. Fusion proteins were expressed in an E. coli host and then purified using preparative SDS-PAGE. One reason for the construction of these fusion proteins was to confirm the absence of a translational stop codon in various regions of the ORF. This aim was addressed by comparison of measured fusion protein molecular weights with those theoretically expected from translational read-through of the entire cloned fhaB inserts. Table 1 lists the fusion proteins with the nucleotide coordinates of the respective fhaB inserts: these data confirm the absence of a stop codon in all of these fhaB fragments.

TABLE 1

|  | Observed MW | FRAGMENT |
| --- | --- | --- |
| protein H1 | 45 Kda | BamHI-RsaI 2836-3786 |
| protein H2 | 85 Kda | BamHI-NruI 5212-7294 |
| protein H3 | 77 Kda | PvuII-PvuII 6393-8085 |
| protein H4 | 80 Kda | PvuII-BamHI 8085-9922 |

TABLE 1-continued

|  | Observed MW | FRAGMENT |
| --- | --- | --- |
| protein H5 | 55 Kda | StuI-BamHI 8752-9922 |
| protein H6 | 32 Kda | EcoRV-BamHI 9462-9922 |
| protein H7 | 56 Kda | BamHI-ClaI 9922-11666 |

Western Immunoblot Analysis using Fusion Protein Antisera

Antisera to each of the seven fusion proteins were prepared by intraperitoneal immunisation of mice and were used for two purposes: to correlate each of the FHA SDS-PAGE bands with a region of the fhaB ORF, and to determine what portions of ORF-encoded polypeptide are present in whole Bordetella sp. extracts. Table 2 shows the results of Western immunoblots using each of the seven fusion protein antisera and an FHA protein gel pattern.

The combination of these data with the results of N-terminal amino acid sequencing suggest an origin for the different FHA polypeptide species. The stimulation of a murine polyclonal response by each of the fhaB fusion proteins also argues that FHA contains numerous immunogenic domains.

TABLE 2

|  | Polyclonal Sera | | | | | | | |
| --- | --- | --- | --- | --- | --- | --- | --- | --- |
| FHA | anti FHA | anti H1 | anti H2 | anti H3 | anti H4 | anti H5 | anti H6 | anti H7 |
| 30 ----- | + | + | + | − | − | − | − | − |
| 40 ----- | + | + | + | − | − | − | − | − |
| 25 ----- | + | + | + | + | − | − | − | − |
| 98 ----- | + | + | − | − | − | − | − | − |
| 75 ----- | + | − | − | − | − | − | − | − |
| 58 ----- | + | − | − | − | − | − | − | − |

Nucleotide Sequence of the FRA Structural Gene

The sequencing strategy described above yielded a 10036bp-long nucleotide sequence for the EcoRI fragment. Computer analysis identified an open reading frame (ORF) 10789 bp long beginning at an ATG translational start codon 253 bp from the left-hand EcoRI site. Two other in-frame ATG codons are located 45 and 174 bp after the beginning of the ORF; at approximately the position of the third ATG codon begins the use of codons strongly preferred by B. pertussis (defined by B. pertussis pertussis toxin operon codon usage and the UWGCG codon preference program; Gribskov et al., Nucleic Acids Res. (1984) 12:539–549). The ORF and preferred codon usage end at a TAG stop codon 11041 bp from the left-hand EcoRI site. This ORF encompasses the FHA structural gene fhaB; the sequence of the ORF is shown below.

```
GAATTCCTGCGCTGGCACCCGCGGCGGGCCGGGGAGCGGGTTGTCGGCGCA                51

CGCCTATACGTGCCGGACAGGGTTTGATGGTTTGACTAAGAAATTTCCTAC                102

AAGTCTTGTATAAATATCCATTGATGGACGGGATCATTACTGACTGACGAA                153

GTGCTGAGGTTTATCCAGACTATGGCACTGGATTTCAAAACCTAAAACGAG                204

CAGGCCGATAACGGATTCTGCCGATTACTTCACTTCGCTGGTCGGAATATG                255
                                                  Met

AACACGAACCTGTACAGGCTGGTCTTCAGCCATGTTCGCGGCATGCTTGTT                306
AsnThrAsnLeuTyrArgLeuValPheSerHisValArgGlyMetLeuVal

CCCGTGAGCGAGCATTGCACCGTCGGAAACACCTTCTGTGGGCGCACGCGT                357
ProValSerGluHisCysThrValGlyAsnThrPheCysGlyArgThrArg

GGTCAAGCGCGAAGTGGGGCCCGCGCCACGAGCCTGTCCGTAGCGCCCAAT                408
GlyGlnAlaArgSerGlyAlaArgAlaThrSerLeuSerValAlaProAsn

GCGCTGGCCTGGGCCCTGATGTTGGCGTGTACGGGTCTTCCGTTAGTAACG                459
AlaLeuAlaTrpAlaLeuMetLeuAlaCysThrGlyLeuProLeuValThr

CACGCCCAGGGCTTGGTTCCTCAGGGGCAGACACAGGTGCTGCAGGGCGGG                510
HisAlaGlnGlyLeuValProGlnGlyGlnThrGlnValLeuGlnGlyGly

AACAAGGTTCCCGTTGTCAATATCGCCGACCCAAATTCCGGCGGCGTCTCG                561
AsnLysValProValValAsnIleAlaAspProAsnSerGlyGlyValSer

CACAACAAGTTCCAGCAGTTCAACGTCGCCAACCCTGGCGTGGTCTTCAAC                612
HisAsnLysPheGlnGlnPheAsnValAlaAsnProGlyValValPheAsn

AACGGCCTGACCGACGGCGTGTCCAGGATCGGCGGGGCGCTGACCAAGAAC                663
AsnGlyLeuThrAspGlyValSerArgIleGlyGlyAlaLeuThrLysAsn

CCCAACCTGACTCGCCAGGCCTCGGCCATTCTTGCCGAAGTCACGGACACT                714
ProAsnLeuThrArgGlnAlaSerAlaIleLeuAlaGluValThrAspThr

TCGCCCAGTCGCCTGGCCGGTACGCTCGAAGTCTATGGCAAGGGCGCCGAC                765
SerProSerArgLeuAlaGlyThrLeuGluValTyrGlyLysGlyAlaAsp

CTCATCATCGCCAACCCCAACGGCATCAGCGTCAACGGCCTGAGCACGCTC                816
LeuIleIleAlaAsnProAsnGlyIleSerValAsnGlyLeuSerThrLeu

AACGCCAGCAACCTGACGCTCACGACGGGGCGTCCCAGCGTCAACGGCGGC                867
AsnAlaSerAsnLeuThrLeuThrThrGlyArgProSerValAsnGlyGly

CGCATCGGCCTTGATGTCCAACAGGGCACCGTCACGATCGAACGAGGCGGC                918
ArgIleGlyLeuAspValGlnGlnGlyThrValThrIleGluArgGlyGly

GTCAATGCCACCGGCCTGGGCTATTTCGACGTGGTGGCGCGCCTGGTCAAG                969
ValAsnAlaThrGlyLeuGlyTyrPheAspValValAlaArgLeuValLys

CTGCAGGGTGCCGTGTCGAGCAAGCAGGGCAAGCCCCTGGCCGACATCGCG                1020
LeuGlnGlyAlaValSerSerLysGlnGlyLysProLeuAlaAspIleAla

GTGGTCGCCGGCGCCAACCGGTACGACCACGCAACCCGCCGCGCCACGCCG                1071
ValValAlaGlyAlaAsnArgTyrAspHisAlaThrArgArgAlaThrPro

ATCGCCGCAGGCGCGCGCGGCGCCGCCGCGGGCGCCTACGCGATTGACGGC                1122
IleAlaAlaGlyAlaArgGlyAlaAlaAlaGlyAlaTyrAlaIleAspGly

ACGGCGGCGGGCGCCATGTACGGCAAGCACATCACGCTGGTGTCCAGCGAT                1173
ThrAlaAlaGlyAlaMetTyrGlyLysHisIleThrLeuValSerSerAsp

TCAGGCCTGGGCGTGCGCCAGCTCGGCAGCCTGTCCTCGCCATCGGCCATC                1224
SerGlyLeuGlyValArgGlnLeuGlySerLeuSerSerProSerAlaIle

ACCGTGTCGTCGCAGGGCGAAATCGCGCTGGGCGACGCCACGGTCCAGCGC                1275
ThrValSerSerGlnGlyGluIleAlaLeuGlyAspAlaThrValGlnArg

GGCCCGCTCAGCCTCAAGGGCGCGGGGGTCGTGTCGGCCGGCAAACTGGCC                1326
GlyProLeuSerLeuLysGlyAlaGlyValValSerAlaGlyLysLeuAla

TCCGGGGGGGGCGGTGAACGTCGCGGGCGGCGGGGCGGTGAAGATCGCG                  1377
SerGlyGlyGlyAlaValAsnValAlaGlyGlyGlyAlaValLysIleAla

TCGGCCAGCAGCGTTGGAAACCTCGCGGTGCAAGGCGGCGGCAAGGTACAG                1428
SerAlaSerSerValGlyAsnLeuAlaValGlnGlyGlyGlyLysValGln
```

```
                                   -continued
GCCACGCTGTTGAATGCCGGGGGACGTTGCTGGTGTCGGGCCGCCAGGCC          1479
AlaThrLeuLeuAsnAlaGlyGlyThrLeuLeuValSerGlyArgGlnAla GTCCAGCTTGGCGCGGCGAGCAGCCGTCAGGCGCTGTCCGTGAACGCGGGC          1530
ValGlnLeuGlyAlaAlaSerSerArgGlnAlaLeuSerValAsnAlaGly GGCGCCCTCAAGGCGGACAAGCTGTCGGCGACGCGACGGGTCGACGTGGAT          1581
GlyAlaLeuLysAlaAspLysLeuSerAlaThrArgArgValAspValAsp GGCAAGCAGGCCGTCGCGCTGGGGTCGGCCAGCAGCAATGCGCTGTCGGTG          1632
GlyLysGlnAlaValAlaLeuGlySerAlaSerSerAsnAlaLeuSerVal CGTGCCGGCGGCGCCCTCAAGGCGGGCAAGCTGTCGGCGACGGGGCGACTG          1683
ArgAlaGlyGlyAlaLeuLysAlaGlyLysLeuSerAlaThrGlyArgLeu GACGTGGACGGCAAGCAGGCCGTCACGCTGGGTTCGGTTGCGAGCGACGGT          1734
AspValAspGlyLysGlnAlaValThrLeuGlySerValAlaSerAspGly GCGCTGTCGGTAAGCGCTGGCGGAAACCTGCGGGCGAACGAATTGGTCTCC          1785
AlaLeuSerValSerAlaGlyGlyAsnLeuArgAlaAsnGluLeuValSer AGTGCCCAACTTGAGGTGCGTGGGCAGCGGGAGGTCGCGCTGGATGACGCT          1836
SerAlaGlnLeuGluValArgGlyGlnArgGluValAlaLeuAspAspAla TCGAGCGCACGCGGCATGACCGTGGTTGCCGCAGGAGCGCTGGCGGCCCGC          1887
SerSerAlaArgGlyMetThrValValAlaAlaGlyAlaLeuAlaAlaArg AACCTGCAGTCCAAGGGCGCCATCGGCGTACAGGGTGGAGAGGCGGTCAGC          1938
AsnLeuGlnSerLysGlyAlaIleGlyValGlnGlyGlyGluAlaValSer GTGGCCAACGCGAACAGCGACGCGGAATTGCGCGTGCGCGGGCGCGGCCAG          1989
ValAlaAsnAlaAsnSerAspAlaGluLeuArgValArgGlyArgGlyGln GTGGATCTGCACGACCTGAGCGCAGCGCGCGGCGCGGATATCTCCGGCGAG          2040
ValAspLeuHisAspLeuSerAlaAlaArgGlyAlaAspIleSerGlyGlu GGGCGCGTCAATATCGGCCGTGCGCGCAGCGATAGCGATGTGAAGGTCTCC          2091
GlyArgValAsnIleGlyArgAlaArgSerAspSerAspValLysValSer GCGCACGGCGCCTTGTCGATCGATAGCATGACGGCCCTCGGTGCGATCGGC          2142
AlaHisGlyAlaLeuSerIleAspSerMetThrAlaLeuGlyAlaIleGly GTCCAGGCAGGCGGCAGCGTGTCGGCCAAGGATATGCGCAGCCGTGGCGCC          2193
ValGlnAlaGlyGlySerValSerAlaLysAspMetArgSerArgGlyAla GTCACCGTCAGCGGCGGCGGCGCCGTCAACCTGGGCGATGTCCAGTCGGAT          2244
ValThrValSerGlyGlyGlyAlaValAsnLeuGlyAspValGlnSerAsp GGGCAGGTCCGCGCCACCAGCGCGGGCGCCATGACGGTGCGAGACGTCGCG          2295
GlyGlnValArgAlaThrSerAlaGlyAlaMetThrValArgAspValAla GCTGCCGCCGACCTTGCGCTGCAGGCGGGCGACGCGTTGCAGGCCGGGTTC          2346
AlaAlaAlaAspLeuAlaLeuGlnAlaGlyAspAlaLeuGlnAlaGlyPhe CTGAAATCGGCCGGTGCCATGACCGTGAACGGCCGCGATGCCGTGCGACTG          2397
LeuLysSerAlaGlyAlaMetThrValAsnGlyArgAspAlaValArgLeu GATGGCGCGCACGCGGGCGGGCAATTGCGGGTTTCCAGCGACGGGCAGGCT          2448
AspGlyAlaHisAlaGlyGlyGlnLeuArgValSerSerAspGlyGlnAla GCGTTGGGCAGTCTCGCGGCCAAGGGCGAGCTGACGGTATCGGCCGCGCGC          2499
AlaLeuGlySerLeuAlaAlaLysGlyGluLeuThrValSerAlaAlaArg GCGGCGACCGTGGCCGAGTTGAAGTCGCTGGACAACATCTCCGTGACGGGC          2550
AlaAlaThrValAlaGluLeuLysSerLeuAspAsnIleSerValThrGly GGCGAACGCGTGTCGGTTCAGAGCGTCAACAGCGCGTCCAGGGTCGCCATT          2601
GlyGluArgValSerValGlnSerValAsnSerAlaSerArgValAlaIle TCGGCGCACGGCGCGCTGGATGTAGGCAAGGTTTCCGCCAAGAGCGGTATC          2652
SerAlaHisGlyAlaLeuAspValGlyLysValSerAlaLysSerGlyIle GGGCTCGAAGGCTGGGGCGCGGTCGGAGCGGACTCCCTCGGTTCCGACGGC          2703
GlyLeuGluGlyTrpGlyAlaValGlyAlaAspSerLeuGlySerAspGly GCGATCAGCGTGTCCGGGCGCGATGCGGTCAGGGTCGATCAAGCCCGCAGT          2754
AlaIleSerValSerGlyArgAspAlaValArgValAspGlnAlaArgSer CTTGCCGACATTTCGCTGGGGGCGGAAGGCGGCGCCACGCTGGGCGCGGTG          2805
LeuAlaAspIleSerLeuGlyAlaGluGlyGlyAlaThrLeuGlyAlaVal
```

```
GAGGCCGCCGGTTCGATCGACGTGCGCGGCGGATCCACGGTGGCGGCGAAC      2856
GluAlaAlaGlySerIleAspValArgGlyGlySerThrValAlaAlaAsn

TCGCTGCACGCCAATCGCGACGTTCGGGTCAGCGGCAAGGATGCGGTGCGC      2907
SerLeuHisAlaAsnArgAspValArgValSerGlyLysAspAlaValArg

GTAACGGCCGCCACCAGCGGGGCGGTCTGCATGTGTCGAGCGGCCGCCAG       2958
ValThrAlaAlaThrSerGlyGlyGlyLeuHisValSerSerGlyArgGln

CTCGATCTGGGCGCCGTGCAGGCGCGCGGCGCGCTGGCCCTGGACGGAGGC      3009
LeuAspLeuGlyAlaValGlnAlaArgGlyAlaLeuAlaLeuAspGlyGly

GCCGGCGTGGCGCTGCAATCGGCCAAGGCTAGCGGCACGCTGCATGTGCAG      3060
AlaGlyValAlaLeuGlnSerAlaLysAlaSerGlyThrLeuHisValGln

GGCGGCGAGCACCTGGACCTGGGCACGTTGGCCGCCGTAGGGGCGGTGGAC      3111
GlyGlyGluHisLeuAspLeuGlyThrLeuAlaAlaValGlyAlaValAsp

GTCAATGGCACGGGAGACGTGCGCGTTGCGAAGCTGGTGAGCGATGCAGGC      3162
ValAsnGlyThrGlyAspValArgValAlaLysLeuValSerAspAlaGly

GCCGATCTGCAAGCGGGGCGCTCCATGACGCTGGGTATCGTCGACACGACC      3213
AlaAspLeuGlnAlaGlyArgSerMetThrLeuGlyIleValAspThrThr

GGCGATCTGCAGGCGCGCGCGCAGCAGAAGCTGGAGCTCGGGTCGGTTAAG     3264
GlyAspLeuGlnAlaArgAlaGlnGlnLysLeuGluLeuGlySerValLys

AGCGATGGCGGCCTTCAGGCGGCCGCCGGCGGGGCCCTCAGCCTGGCGGCG     3315
SerAspGlyGlyLeuGlnAlaAlaAlaGlyGlyAlaLeuSerLeuAlaAla

GCGGAAGTCGCAGGGGCGCTGGAGCTCTCGGGCCAGGGCGTCACCGTGGAC     3366
AlaGluValAlaGlyAlaLeuGluLeuSerGlyGlnGlyValThrValAsp

AGAGCCAGCGCTAGCCGGGCACGCATCGACAGCACCGGTTCGGTCGGCATC     3417
ArgAlaSerAlaSerArgAlaArgIleAspSerThrGlySerValGlyIle

GGCGCGCTGAAGGCAGGCGCTGTCGAGGCCGCCTCGCCACGGCGGGCGCGC     3468
GlyAlaLeuLysAlaGlyAlaValGluAlaAlaSerProArgArgAlaArg

CGCGCGCTGCGGCAGGATTTCTTCACGCCCGGCAGCGTGGTGGTCCGCGCC     3519
ArgAlaLeuArgGlnAspPhePheThrProGlySerValValValArgAla

CAGGGCAATGTCACGGTCGGGCGCGGCGATCCGCATCAGGGCGTGCTGGCC     3570
GlnGlyAsnValThrValGlyArgGlyAspProHisGlnGlyValLeuAla

CAGGGCGACATCATCATGGATGCGAAGGGCGGCACCTTGCTGTTGCGCAAC     3621
GlnGlyAspIleIleMetAspAlaLysGlyGlyThrLeuLeuLeuArgAsn

GATGCCTTGACCGAGAACGGGACGGTCACCATATCGGCCGATTCGGCCGTG     3672
AspAlaLeuThrGluAsnGlyThrValThrIleSerAlaAspSerAlaVal

CTCGAGCATTCCACCATCGAGAGCAAGATCAGCCAGAGCGTGCTGGCTGCC     3723
LeuGluHisSerThrIleGluSerLysIleSerGlnSerValLeuAlaAla

AAAGGGGACAAGGGCAAGCCGGCGGTGTCGGTGAAGGTCGCGAAGAAGCTG     3774
LysGlyAspLysGlyLysProAlaValSerValLysValAlaLysLysLeu

TTTCTCAATGGTACGTTGCGGGCCGTCAACGACAACAACGAAACCATGTCC     3825
PheLeuAsnGlyThrLeuArgAlaValAsnAspAsnAsnGluThrMetSer

GGGCGCCAGATCGACGTCGTGGACGGACGTCCGCAGATCACCGACGCGGTC     3876
GlyArgGlnIleAspValValAspGlyArgProGlnIleThrAspAlaVal

ACGGGCGAAGCGCGTAAGGACGAATCGGTTGTGTCCGACGCCGCGCTCGTG     3927
ThrGlyGluAlaArgLysAspGluSerValValSerAspAlaAlaLeuVal

GCCGATGGCGGTCCGATCGTGGTCGAGGCCGGCGAGCTGGTCAGCCATGCC     3978
AlaAspGlyGlyProIleValValGluAlaGlyGluLeuValSerHisAla

GGCGGTATCGGCAACGGCCGCAACAAGGAGAATGGCGCCAGCGTCACCGTG     4029
GlyGlyIleGlyAsnGlyArgAsnLysGluAsnGlyAlaSerValThrVal

CGCACGACTGGCAACCTGGTCAACAAGGGCTACATCTCGGCCGGCAAGCAG     4080
ArgThrThrGlyAsnLeuValAsnLysGlyTyrIleSerAlaGlyLysGln

GGCGTGCTCGAGGTGGGCGGCGCCTTGACGAACGAGTTCCTGGTCGGCTCG     4131
GlyValLeuGluValGlyGlyAlaLeuThrAsnGluPheLeuValGlySer
```

-continued

```
GACGGCACCCAGCGCATCGAGGCGCAGCGCATCGAGAACAGGGGCACCTTC      4182
AspGlyThrGlnArgIleGluAlaGlnArgIleGluAsnArgGlyThrPhe

CAGAGCCAGGCTCCGGCGGGCACGGCCGGCGCCCTGGTGGTCAAGGCTGCC      4233
GlnSerGlnAlaProAlaGlyThrAlaGlyAlaLeuValValLysAlaAla

GAGGCCATCGTGCACGACGGCGTCATGGCCACCAAAGGCGAGATGCAGATC      4284
GluAlaIleValHisAspGlyValMetAlaThrLysGlyGluMetGlnIle

GCCGGCAAGGGCGGCGGGTCTCCGACCGTCACCGCCGGCGCAAAGGCGACG      4335
AlaGlyLysGlyGlyGlySerProThrValThrAlaGlyAlaLysAlaThr

ACCAGCGCGAACAAGCTGAGCGTCGACGTGGCAAGCTGGGACAACGCGGGA      4386
ThrSerAlaAsnLysLeuSerValAspValAlaSerTrpAspAsnAlaGly

AGCCTGGATATCAAGAAGGGCGGCGCGCAGGTCACGGTGGCCGGCGCGCTAT    4437
SerLeuAspIleLysLysGlyGlyAlaGlnValThrValAlaGlyArgTyr

GCCGAGCACGGCGAGGTTTCGATACAGGGCGATTACACCGTCTCGGCCGAC     4488
AlaGluHisGlyGluValSerIleGlnGlyAspTyrThrValSerAlaAsp

GCCATCGCGCTGGCGGCGCAGGTCACCCAGCGCGGAGGCGCCGCGAACCTG     4539
AlaIleAlaLeuAlaAlaGlnValThrGlnArgGlyGlyAlaAlaAsnLeu

ACCTCGCGGCACGACACCCGTTTCTCCAACAAGATTCGCCTGATGGGGCCG     4590
ThrSerArgHisAspThrArgPheSerAsnLysIleArgLeuMetGlyPro

TTGCAGGTCAACGCCGGCGGGCCGGTGTCCAATACCGGCAATCTGAAAGTG     4641
LeuGlnValAsnAlaGlyGlyProValSerAsnThrGlyAsnLeuLysVal

CGCGAGGGCGTGACCGTAACGGCGGCGTCGTTCGACAACGAGACCGGGGCC     4692
ArgGluGlyValThrValThrAlaAlaSerPheAspAsnGluThrGlyAla

GAGGTCATGGCCAAGAGCGCCACGCTGACGACTTCCGGGGCCGCGCGCAAC     4743
GluValMetAlaLysSerAlaThrLeuThrThrSerGlyAlaAlaArgAsn

GCGGGCAAGATGCAGGTCAAGGAGGCCGCCACGATCGTTGCCGCCAGCGTT     4794
AlaGlyLysMetGlnValLysGluAlaAlaThrIleValAlaAlaSerVal

TCCAATCCCGGCACGTTCACGGCCGGCAAGGATATCACTGTTACCTCGCGC     4845
SerAsnProGlyThrPheThrAlaGlyLysAspIleThrValThrSerArg

GGAGGATTCGATAACGAAGGCAAGATGGAGTCCAACAAGGACATCGTCATC     4896
GlyGlyPheAspAsnGluGlyLysMetGluSerAsnLysAspIleValIle

AAGACGGAACAGTTCAGCAATGGCAGGGTTCTCGACGCCAAGCATGATCTG     4947
LysThrGluGlnPheSerAsnGlyArgValLeuAspAlaLysHisAspLeu

ACGGTCACGGCGAGCGGGCAGGCGGACAACCGGGGCAGCCTGAAGGCAGGC    4998
ThrValThrAlaSerGlyGlnAlaAspAsnArgGlySerLeuLysAlaGly

CACGATTTCACGGTGCAGGCCCAGCGTATCGACAATAGCGGAACCATGGCC    5049
HisAspPheThrValGlnAlaGlnArgIleAspAsnSerGlyThrMetAla

GCCGGCCACGACGCCACGCTGAAGGCGCCGCACCTGCGCAATACGGGCCAG    5100
AlaGlyHisAspAlaThrLeuLysAlaProHisLeuArgAsnThrGlyGln

GTCGTAGCCGGGCACGACATCCATATCATCAACAGCGCCAAGCTGGAGAAC    5151
ValValAlaGlyHisAspIleHisIleIleAsnSerAlaLysLeuGluAsn

ACCGGGCGCGTGGATGCGCGCAACGACATCGCTCTGGATGTGGCGGATTTC    5202
ThrGlyArgValAspAlaArgAsnAspIleAlaLeuAspValAlaAspPhe

ACCAACACGGGATCCCTCTACGCCGAGCATGACGCGACGCTGACGCTTGCG    5253
ThrAsnThrGlySerLeuTyrAlaGluHisAspAlaThrLeuThrLeuAla

CAAGGCACGCAGCGCGATCTGGTGGTGGACCAGGATCATATCCTGCCGGTG    5304
GlnGlyThrGlnArgAspLeuValValAspGlnAspHisIleLeuProVal

GCGGAGGGGACGTTACGCGTCAAGGCCAAGTCGCTGACCACCGAAATCGAG    5355
AlaGluGlyThrLeuArgValLysAlaLysSerLeuThrThrGluIleGlu

ACCGGCAATCCCGGCAGCCTGATCGCCGAGGTGCAGGAAAATATCGACAAC    5406
ThrGlyAsnProGlySerLeuIleAlaGluValGlnGluAsnIleAspAsn

AAGCAGGCCATCGTCGTCGGCAAGGACCTGACGCTGAGTTCGGCGCACGGC    5457
LysGlnAlaIleValValGlyLysAspLeuThrLeuSerSerAlaHisGly

AACGTGGCCAACGAAGCGAACGCGCTGCTGTGGGCCGCCGGGGAGCTGACC    5508
AsnValAlaAsnGluAlaAsnAlaLeuLeuTrpAlaAlaGlyGluLeuThr
```

-continued

```
GTCAAGGCGCAGAACATCACCAATAAACGGGCCGCGCTGATCGAGGCGGGC    5559
ValLysAlaGlnAsnIleThrAsnLysArgAlaAlaLeuIleGluAlaGly

GGCAACGCCCGGCTGACGGCGGCCGTTGCCTTGCTCAACAAGCTGGGCCGC    5610
GlyAsnAlaArgLeuThrAlaAlaValAlaLeuLeuAsnLysLeuGlyArg

ATTCGCGCGGGCGAGGACATGCACCTGGATGCGCCGCGCATCGAGAACACC    5661
IleArgAlaGlyGluAspMetHisLeuAspAlaProArgIleGluAsnThr

GCGAAACTGAGCGGCGAGGTGCAACGCAAAGGCGTGCAGGACGTCGGGGGA    5712
AlaLysLeuSerGlyGluValGlnArgLysGlyValGlnAspValGlyGly

GGCGAGCACGGCCGCTGGAGCGGTATCGGCTATGTCAACTACTGGTTGCGC    5763
GlyGluHisGlyArgTrpSerGlyIleGlyTyrValAsnTyrTrpLeuArg

GCCGGCAATGGGAAGAAGGCGGGAACCATCGCCGCGCCGTGGTATGGCGGT    5814
AlaGlyAsnGlyLysLysAlaGlyThrIleAlaAlaProTrpTyrGlyGly

GATCTGACGGCGGAGCAGTCGCTCATCGAGGTCGGCAAGGATCTCTATCTG    5865
AspLeuThrAlaGluGlnSerLeuIleGluValGlyLysAspLeuTyrLeu

AATGCCGGAGCGCGCAAGGACGAACATCGCCATCTGCTCAATGAAGGCGTG    5916
AsnAlaGlyAlaArgLysAspGluHisArgHisLeuLeuAsnGluGlyVal

ATCCAGGCGGGCGGCCATGGCCACATCGGCGGCGACGTGGACAACCGGTCG    5967
IleGlnAlaGlyGlyHisGlyHisIleGlyGlyAspValAspAsnArgSer

GTGGTGCGCACCGTGTCCGCCATGGAGTATTTCAAGACGCCTCTTCCGGTG    6018
ValValArgThrValSerAlaMetGluTyrPheLysThrProLeuProVal

AGCCTGACTGCCCTGGACAATCGTGCCGGCTTGTCTCCGGCGACCTGGAAC    6069
SerLeuThrAlaLeuAspAsnArgAlaGlyLeuSerProAlaThrTrpAsn

TTCCAGTCCACGTATGAACTCCTGGATTATCTGCTGGACCAGAATCGCTAC    6120
PheGlnSerThrTyrGluLeuLeuAspTyrLeuLeuAspGlnAsnArgTyr

GAGTACATTTGGGGGCTGTATCCGACCTACACCGAATGGTCGGTGAATACG    6171
GluTyrIleTrpGlyLeuTyrProThrTyrThrGluTrpSerValAsnThr

CTGAAGAACCTCGACCTGGGCTACCAGGCCAAGCCGGCTCCCACTGCGCCG    6222
LeuLysAsnLeuAspLeuGlyTyrGlnAlaLysProAlaProThrAlaPro

CCGATGCCCAAGGCTCCCGAACTCGACCTGCGTGGCCATACGCTGGAGTCG    6273
ProMetProLysAlaProGluLeuAspLeuArgGlyHisThrLeuGluSer

GCCGAAGGCCGGAAGATCTTTGGCGAGTACAAGAAGCTGCAAGGCGAGTAC    6324
AlaGluGlyArgLysIlePheGlyGluTyrLysLysLeuGlnGlyGluTyr

GAGAAGGCGAAGATGGCCGTCCAGGCCGTGGAGGCTTACGGCGAGGCTACT    6375
GluLysAlaLysMetAlaValGlnAlaValGluAlaTyrGlyGluAlaThr

CGGCGCGTCCATGATCAGCTGGGCCAACGTTATGGTAAGGCCCTGGGCGGC    6426
ArgArgValHisAspGlnLeuGlyGlnArgTyrGlyLysAlaLeuGlyGly

ATGGATGCCGAGACCAAGGAGGTCGACGGCATCATCCAGGAGTTCGCCGCG    6477
MetAspAlaGluThrLysGluValAspGlyIleIleGlnGluPheAlaAla

GATCTGCGAACGGTCTATGCGAAGCAGGCCGACCAGGCGACCATCGACGCA    6528
AspLeuArgThrValTyrAlaLysGlnAlaAspGlnAlaThrIleAspAla

GAGACGGACAAGGTCGCCCAGCGCTACAAGTCGCAGATCGACGCGGTGCGG    6579
GluThrAspLysValAlaGlnArgTyrLysSerGlnIleAspAlaValArg

CTGCAGGCGATCCAGCCTGGCCGGGTCACGCTGGCCAAGGCGCTGTCGGCG    6630
LeuGlnAlaIleGlnProGlyArgValThrLeuAlaLysAlaLeuSerAla

GCGCTGGGCGCCGACTGGCGCGCGCTGGGTCACTCCCAATTGATGCAGCGC    6681
AlaLeuGlyAlaAspTrpArgAlaLeuGlyHisSerGlnLeuMetGlnArg

TGGAAGGATTTCAAGGCGGGCAAGCGCGGCGCGGAAATCGCGTTCTATCCC    6732
TrpLysAspPheLysAlaGlyLysArgGlyAlaGluIleAlaPheTyrPro

AAGGAACAAACCGTGCTGGCCGCCGGCGCCGGTTTGACCCTGTCCAACGGG    6783
LysGluGlnThrValLeuAlaAlaGlyAlaGlyLeuThrLeuSerAsnGly

GCGATCCACAACGGCGAGAACGCCGCGCAGAATCGCGGCCGGCCGGAAGGC    6834
AlaIleHisAsnGlyGluAsnAlaAlaGlnAsnArgGlyArgProGluGly
```

-continued

```
CTGAAAATCGGCGCACATTCGGCGACTTCGGTGAGCGGCTCGTTCGACGCC       6885
LeuLysIleGlyAlaHisSerAlaThrSerValSerGlySerPheAspAla

TTGCGCGACGTGGGGCTGGAAAAGCGGCTGGATATCGACGATGCGCTGGCT       6936
LeuArgAspValGlyLeuGluLysArgLeuAspIleAspAspAlaLeuAla

GCCGTGCTCGTGAATCCGCATATTTTCACGCGGATCGGGGCGGCTCAGACA       6987
AlaValLeuValAsnProHisIlePheThrArgIleGlyAlaAlaGlnThr

TCCCTTGCCGACGGCGCCGCCGGGCCGGCGCTGGCGCGCCAGGCCAGGCAA       7038
SerLeuAlaAspGlyAlaAlaGlyProAlaLeuAlaArgGlnAlaArgGln

GCGCCGGAGACCGACGGCATGGTGGATGCGCGAGGGCTGGGCAGCGCCGAT       7089
AlaProGluThrAspGlyMetValAspAlaArgGlyLeuGlySerAlaAsp

GCGCTCGCTTCCCTGGCCAGCTTGGACGCGGCGCAAGGGCTGGAGGTATCC       7140
AlaLeuAlaSerLeuAlaSerLeuAspAlaAlaGlnGlyLeuGluValSer

GGCAGGCGCAATGCGCAGGTGGCCGACGCCGGGCTCGCCGGGCCGAGCGCC       7191
GlyArgArgAsnAlaGlnValAlaAspAlaGlyLeuAlaGlyProSerAla

GTCGCGGCGCCGGCCGTCGGGGCGGCCGATGTCGGCGTGGAGCCTGTCACG       7242
ValAlaAlaProAlaValGlyAlaAlaAspValGlyValGluProValThr

GGGGACCAGGTCGACCAGCCTGTCGTGGCGGTCGGGCTCGAGCAGCCTGTC       7293
GlyAspGlnValAspGlnProValValAlaValGlyLeuGluGlnProVal

GCGACGGTCCGGGTCGCGCCGCCAGCCGTCGCGTTGCCGCGGCCGCTGTTC       7344
AlaThrValArgValAlaProProAlaValAlaLeuProArgProLeuPhe

GAAACCCGCATCAAGTTTATCGACCAGAGCAAATTCTACGGCTCGCGTTAT       7395
GluThrArgIleLysPheIleAspGlnSerLysPheTyrGlySerArgTyr

TTCTTCGAGCAGATCGGCTACAAGCCCGATCGCGCCGCGCGGGTGGCGGGC       7446
PhePheGluGlnIleGlyTyrLysProAspArgAlaAlaArgValAlaGly

GACAACTATTTCGATACCACGCTGGTGCGCGAGCAGGTGCGGCGCGCCCTG       7497
AspAsnTyrPheAspThrThrLeuValArgGluGlnValArgArgAlaLeu

GGCGGCTATGAAAGCCGCCTGCCCGTGCGCGGTGTCGCGTTGGTGGCCAAG       7548
GlyGlyTyrGluSerArgLeuProValArgGlyValAlaLeuValAlaLys

CTGATGGATTCGGCCGGGACGGTCGGCAAGGCGCTGGGCCTGAAGGTGGGT       7599
LeuMetAspSerAlaGlyThrValGlyLysAlaLeuGlyLeuLysValGly

GTCGCGCCGACCGCGCAGCAGCTCAAGCAGGCCGACCGCGATTTCGTCTGG       7650
ValAlaProThrAlaGlnGlnLeuLysGlnAlaAspArgAspPheValTrp

TACGTGGATACCGTGATCGACGGCCAGAAGGTTCTCGCTCCCCGGCTGTAC       7701
TyrValAspThrValIleAspGlyGlnLysValLeuAlaProArgLeuTyr

CTGACCGAGGCGACGCGCCAGGGCATCACGGATCAGTACGCCGGCGGCGGG       7752
LeuThrGluAlaThrArgGlnGlyIleThrAspGlnTyrAlaGlyGlyGly

GCGCTGATTGCCTCCGGCGGCGACGTAACTGTCAATACGGACGGCCATGAC       7803
AlaLeuIleAlaSerGlyGlyAspValThrValAsnThrAspGlyHisAsp

GTCAGTTCGGTCAACGGGCTGATCCAGGGCAGGAGCGTCAAGGTGGACGCG       7854
ValSerSerValAsnGlyLeuIleGlnGlyArgSerValLysValAspAla

GGCAAGGGCAAGGTCGTGGTGGCCGACAGCAAGGGGCGGGCGGCGGCATC       7905
GlyLysGlyLysValValValAlaAspSerLysGlyAlaGlyGlyGlyIle

GAGGCCGATGACGAGGTCGACGTCTCAGGCCGGGATATCGGCATCGAGGGC       7956
GluAlaAspAspGluValAspValSerGlyArgAspIleGlyIleGluGly

GGCAAGCTGCGCGGCAAGGATGTCAGGCTCAAGGCCGACACGGTCAAGGTC       8007
GlyLysLeuArgGlyLysAspValArgLeuLysAlaAspThrValLysVal

GCGACCTCGATGCGTTACGACGACAAGGGCAGGCTGGCGGCGCGCGGCGAC       8058
AlaThrSerMetArgTyrAspAspLysGlyArgLeuAlaAlaArgGlyAsp

GGCGCCCTGGATGCGCAAGGCGGCCAGCTGCATATCGAGGCCAAGCGCCTG       8109
GlyAlaLeuAspAlaGlnGlyGlyGlnLeuHisIleGluAlaLysArgLeu

GAGACGGCCGGCGCGACGCTCAAGGGCGGCAAGGTGAAGCTGGATGTCGAT       8160
GluThrAlaGlyAlaThrLeuLysGlyGlyLysValLysLeuAspValAsp

GACGTCAAGTTGGGCGGCGTGTACGAGGCGGGTCCAGCTACGAGAACAAG       8211
AspValLysLeuGlyGlyValTyrGluAlaGlySerSerTyrGluAsnLys
```

-continued

```
AGCTCGACGCCGCTGGGCAGCCTGTTCGCCATCCTGTCGTCGACGACGGAA        8262
SerSerThrProLeuGlySerLeuPheAlaIleLeuSerSerThrThrGlu

ACCAACCAGTCGGCACACGCGAACCATTACGGTACGCGCATCGAAGCCGGT        8313
ThrAsnGlnSerAlaHisAlaAsnHisTyrGlyThrArgIleGluAlaGly

ACGCTGGAAGGAAAGATGCAGAACCTGGAGATCGAAGGCGGTTCGGTCGAT        8364
ThrLeuGluGlyLysMetGlnAsnLeuGluIleGluGlyGlySerValAsp

GCCGCGCATACGGACCTGTCCGTGGCCCGCGACGCGAGGTTCAAGGCCGCC        8415
AlaAlaHisThrAspLeuSerValAlaArgAspAlaArgPheLysAlaAla

GCGGATTTCGCGCACGCCGAGCATGAGAAGGATGTGCGCCAACTGTCCCTG        8466
AlaAspPheAlaHisAlaGluHisGluLysAspValArgGlnLeuSerLeu

GGTGCCAAGGTGGGGCGGGCGGCTACGAGGCGGGCTTCAGCCTGGGCAGC        8517
GlyAlaLysValGlyAlaGlyGlyTyrGluAlaGlyPheSerLeuGlySer

GAAAGCGGTCTGGAAGCGCACGCCGGCCGCGGTATGACCGCGGGCGCTGAA        8568
GluSerGlyLeuGluAlaHisAlaGlyArgGlyMetThrAlaGlyAlaGlu

GTCAAGGTAGGTTATCGGGCATCGCACGAACAGTCCTCGGAAACCGAAAAG        8619
ValLysValGlyTyrArgAlaSerHisGluGlnSerSerGluThrGluLys

TCCTATCGCAACGCGAACCTCAATTTCGGTGGAGGCTCCGTCGAGGCTGGC        8670
SerTyrArgAsnAlaAsnLeuAsnPheGlyGlyGlySerValGluAlaGly

AATGTCCTGGATATCGGCGGCGCCGACATCAACCGGAACCGGTACGGCGGC        8721
AsnValLeuAspIleGlyGlyAlaAspIleAsnArgAsnArgTyrGlyGly

GCCGCGAAGGGGAACGCCGGGACCGAGGAGGCCTTGCGCATGCGCGCCAAG        8772
AlaAlaLysGlyAsnAlaGlyThrGluGluAlaLeuArgMetArgAlaLys

AAGGTCGAGTCCACCAAGTACGTCAGCGAGCAGACGAGCCAGAGCTCCGGC        8823
LysValGluSerThrLysTyrValSerGluGlnThrSerGlnSerSerGly

TGGAGCGTGGAGGTGGCATCGACGGCCAGTGCCCGTTCCAGCCTGCTGACG        8874
TrpSerValGluValAlaSerThrAlaSerAlaArgSerSerLeuLeuThr

GCCGCCACGCGCCTGGGCGACAGCGTGGCGCAGAATGTCGAGGACGGCCGC        8925
AlaAlaThrArgLeuGlyAspSerValAlaGlnAsnValGluAspGlyArg

GAGATCCGCGGCGAGCTGATGGCTGCGCAAGTCGCCGCGGAGGCCACGCAA        8976
GluIleArgGlyGluLeuMetAlaAlaGlnValAlaAlaGluAlaThrGln

CTGGTAACCGCCGACACGCGGCGGTGGCACTGAGTGCCGGAATCAGCGCC        9027
LeuValThrAlaAspThrAlaAlaValAlaLeuSerAlaGlyIleSerAla

GACTTCGACAGCAGCCACAGCCGCTCCACCTCGCAGAATACCCAATATCTG        9078
AspPheAspSerSerHisSerArgSerThrSerGlnAsnThrGlnTyrLeu

GGCGGAAACTTGTCCATCGAGGCCACCGAGGGCGATGCGACGCTGGTGGGC        9129
GlyGlyAsnLeuSerIleGluAlaThrGluGlyAspAlaThrLeuValGly

GCGAAGTTCGGCGGTGGCGACCAGGTCAGCTTGAAGGCAGCGAAGAGCGTG        9180
AlaLysPheGlyGlyGlyAspGlnValSerLeuLysAlaAlaLysSerVal

AACCTCATGGCGGCCGAATCGACCTTCGAATCGTACTCGGAGAGCCACAAC        9231
AsnLeuMetAlaAlaGluSerThrPheGluSerTyrSerGluSerHisAsn

TTCCACGCCTCCGCCGACGCGAACCTTGGCGCCAACGCCGTGCAGGGCGCC        9282
PheHisAlaSerAlaAspAlaAsnLeuGlyAlaAsnAlaValGlnGlyAla

GTTGGCCTGGGGTTGACTGCGGGTATGGGACGTCGCATCAGATTACCAAC        9333
ValGlyLeuGlyLeuThrAlaGlyMetGlyThrSerHisGlnIleThrAsn

GAAACCGGCAAGACCTATGCCGGAACCTCGGTGGATGCGGCGAACGTGTCG        9384
GluThrGlyLysThrTyrAlaGlyThrSerValAspAlaAlaAsnValSer

ATCGATGCAGGCAAGGATCTGAACCTTTCCGGGTCCCGCGTGCGGGGTAAG        9435
IleAspAlaGlyLysAspLeuAsnLeuSerGlySerArgValArgGlyLys

CATGTTGTCCTGGATGTCGAGGGCGATATCAATGCGACCAGCAAGCAGGAT        9486
HisValValLeuAspValGluGlyAspIleAsnAlaThrSerLysGlnAsp

GAACGCAACTACAACTCCAGCGGTGGCGGTTGGGACGCCTCGGCAGGGGTG        9537
GluArgAsnTyrAsnSerSerGlyGlyGlyTrpAspAlaSerAlaGlyVal
```

```
                                  -continued
GCGATTCAGAACCGCACGTTGGTTGCGCCCGTGGGGTCTGCCGGCTTCAAT        9588
AlaIleGlnAsnArgThrLeuValAlaProValGlySerAlaGlyPheAsn TTCAATACGGAACACGACAATTCGCGCCTGACCAATGACGGGGCGGCGGT        9639
PheAsnThrGluHisAspAsnSerArgLeuThrAsnAspGlyAlaAlaGly GTCGTTGCCAGCGACGGGTTGACGGGCCATGTGAAAGGCGACGCCAACCTG       9690
ValValAlaSerAspGlyLeuThrGlyHisValLysGlyAspAlaAsnLeu ACCGGCGCGACCATTGCCGATTTGTCGGGCAAGGGCAATCTCAAGGTCGAC       9741
ThrGlyAlaThrIleAlaAspLeuSerGlyLysGlyAsnLeuLysValAsp GGCGCGGTCAACGCGCAGAACCTGAAAGACTACCGCGACAAGGACGGCGGC       9792
GlyAlaValAsnAlaGlnAsnLeuLysAspTyrArgAspLysAspGlyGly AGCGGCGGCCTGAACGTGGGCATCTCGTCGACCACGCTGGCGCCCACCGTG       9843
SerGlyGlyLeuAsnValGlyIleSerSerThrThrLeuAlaProThrVal GGCGTGGCGTTCGGCAGGGTGGCCGGAGAGGATTATCAGGCCGAGCAGCGC       9894
GlyValAlaPheGlyArgValAlaGlyGluAspTyrGlnAlaGluGlnArg GCCACGATTGACGTCGGTCAAACCAAGGATCCCGCGCGCCTGCAGGTCGGC       9945
AlaThrIleAspValGlyGlnThrLysAspProAlaArgLeuGlnValGly GGCGGCGTCAAGGGTACCCTCAATCAGGACGCCGCGCAGGCCACGGTCGTT       9996
GlyGlyValLysGlyThrLeuAsnGlnAspAlaAlaGlnAlaThrValVal CAGCGCAACAAGCACTGGGCCGGAGGCGGGTCGGAATTCTCGGTGGCTGGC       10047
GlnArgAsnLysHisTrpAlaGlyGlyGlySerGluPheSerValAlaGly AAGTCACTGAAGAAGAAGAACCAGGTCCGCCCGGTGGAGACGCCGACGCCG       10098
LysSerLeuLysLysLysAsnGlnValArgProValGluThrProThrPro GATGTCGTGGATGGACCGCCTAGCCGTCCCACCACGCCGCCCGCGTCGCCG       10149
AspValValAspGlyProProSerArgProThrThrProProAlaSerPro CAGCCGATCCGCGCGACGGTCGAGGTCAGTTCGCCGCCGCCGGTGTCCGTG       10200
GlnProIleArgAlaThrValGluValSerSerProProProValSerVal GCCACGGTCGAAGTCGTGCCGCGGCCGAAGGTCGAAACCGGCTCAGCCGCT       10251
AlaThrValGluValValProArgProLysValGluThrGlySerAlaAla TCCGCCTCGGCCGGTGGCGCCCAGGTCGTGCCGGTGACGCCTCCCAAGGTG      10302
SerAlaSerAlaGlyGlyAlaGlnValValProValThrProProLysVal GAGGTCGCCAAGGTGGAGGTCGCCAAGGTGGAAGTCGTGCCGCGGCCGAAG      10353
GluValAlaLysValGluValAlaLysValGluValValProArgProLys GTTGAAACGGCTCAGCCGCTTCCGCCCCGGCCGGTGGTGGCCGAGAAGGTG      10404
ValGluThrAlaGlnProLeuProProArgProValValAlaGluLysVal ACGACGCCGGCGGTCCAGCCCCAGCTTGCCAAGGTGGAGACGGTGCAGCCG      10455
ThrThrProAlaValGlnProGlnLeuAlaLysValGluThrValGlnPro GTGAAGCCCGAAACCACCAAGCCGTTGCCCAAGCCGCTGCCGGTGGCGAAG      10506
ValLysProGluThrThrLysProLeuProLysProLeuProValAlaLys GTGACGAAAGCGCCGCCGCCGGTTGTGGAGACCGCCCAGCCGCTGCCGCCG      10557
ValThrLysAlaProProProValValGluThrAlaGlnProLeuProPro GTCAAGCCACAGAAGGCGACCCCCGGCCCCGTGGCTGAGGTGGGCAAGGCT      10608
ValLysProGlnLysAlaThrProGlyProValAlaGluValGlyLysAla ACGGTCACGACGGTGCAGGTGCAGAGTGCGCCGCCCAAGCCGGCCCCGGTG      10659
ThrValThrThrValGlnValGlnSerAlaProProLysProAlaProVal GCCAAGCAGCCCGCGCCTGCACCGAAGCCCAAGCCCAAGCCCAAGCCCAAG      10710
AlaLysGlnProAlaProAlaProLysProLysProLysProLysProLys GCCGAGCGTCCGAAGCCGGGCAAAACGACGCCCTTGAGCGGGCGCCACGTG      10761
AlaGluArgProLysProGlyLysThrThrProLeuSerGlyArgHisVal GTGCAACAGCAGGTGCAGGTCTTGCAGCGGCAAGCGAGTGACATCAACAAC      10812
ValGlnGlnGlnValGlnValLeuGlnArgGlnAlaSerAspIleAsnAsn ACCAAGAGCCTGCCTGGCGGGAAGCTGCCCAAGCCGGTCACCGTGAAGCTG      10863
ThrLysSerLeuProGlyGlyLysLeuProLysProValThrValLysLeu ACCGACGAGAACGGCAAGCCGCAGACGTATACGATCAACCGGCGCGAGGAT      10914
ThrAspGluAsnGlyLysProGlnThrTyrThrIleAsnArgArgGluAsp
```

-continued

```
CTGATGAAGCTCAACGGCAAGGTGCTGTCCACCAAGACGACACTGGGCCTG    10965
LeuMetLysLeuAsnGlyLysValLeuSerThrLysThrThrLeuGlyLeu

GAGCAGACCTTCCGCCTGCGGTCGAGGATATCGGCGGCAAGAACTACCGGG    11016
GluGlnThrPheArgLeuArgSerArgIleSerAlaAlaArgThrThrGly

TCTTCTATGAAACCAACAAATAGGTAGTCGCGGCCTGCCGCGGCTCGGCGC    11067
SerSerMetLysProThrAsnArg

ATGGGGATTCGCAGGGTTCTCATGCGCCGGCCAATGCCGGATAGCGGTGCA    11118

ATTGCCGACCATTTCGCGCACCGCGCTCAAGGACGTAGGGTCGACGGCAGG    11169

CGGGACAGTTTTTGACGTGAAACTGACCGAGTGTCCGCAGGCATTGAATGG    11220

TCAGCAAGTGGGATTGTTCTTCGAATCTGGTGGCACGGTTGACTATACGTC    11271

GGGAAACCTGTTTGCGTATCGGGCCGATAGTCAGGGCGTCGAACAGGCTAC    11322

CGCAGAGCGAAAGCCGACAACGTGCAAGCCAATCTGGATGGTTCCGCTATT    11373

CATTTGGGCCGCAACAAGGGTGCGCAGGCTGCTCAGACGTTTCTGGTATCG    11424

CAGACGGCTGGGTCGTCGACGTACGGGGCGACCCTGCGCTATCTGGCATGC    11475

TACATCCGTTCGGGCGCTGGTTCCATTGTTGCGGGGAATCTCCGCAGTCAG    11526

GTGGGGTTCTCCGTGATGTATCCGTAGCCCGTGAAAGAGGGGTCACCCACT    11577

GCGGGGGCCCCGGTACGGGATGGTCGGCTTGTCACGAGATTCTTGTTTTC    11628

CATTTCTTTCTTTTCACTCGGTCGCAGCGCCGGCTTGATGCATGCAAAGCA    11679

TCGATAGCTACGAACGGCCGCGATTCTTGAATCATGAATACATACGCTTGT    11730

GACGGGGCGCTCGCGAGAGCCGGCCCCAGGGATGGTTTACGCCTGCATTTA    11781

CGGTAAAGCGGCAAGGCGGCATGGCGCGCTGGCGGCGGCTGGGCGTCGCGG    11832

CGCTGGGCCATGCTGGCGAGCCTGGCGCCGGCCGCnCGGGCAGCTyGTnAT    11883
```

The relative GC content of the FHA ORF is 67.5%. Examination of this nucleotide sequence for transcriptional start signals indicates possible –35 and –10 consensus regions, TGGTTTGAC and TATAAAT, separated by 23 base pairs, located 174 and 142 bp upstream of the beginning of the ORF, with transcriptional initiation beginning apparently to 30 to 75 bp from the initiation condon. A possible ribosomal binding site, GAGG, occurs 90 bp upstream of the ORF. Another possible ribosomal binding site, CTGGR occurs 11 bp in front of the third ATG. Further analysis of the nucleotide sequence reveals a region of alternating direct repeats of the pattern, ABABA, located between 1468 and 1746 bp from the left hand EcoRI site. Similar repeats are found in the predicted amino acid sequence corresponding to this same region.

Predicted Peptide Sequence

The predicted amino acid sequence of the FHA ORP is 3597 residues long, with a calculated MW of 368 kDa. This is substantially larger than published measured values. The composition of this sequence is alanine and glycine rich (27.0%) and is nearly identical to a previously published chemical analysis of the FHA amino acid composition (Sato et al., 1983, supra). The computed isoelectric point of the entire polypeptide is 6.79.

The concentration of charged residues in the FRA polypeptide chain is highest between positions 2000 and 2700. Hydrophobicity is highest in the N-terminal 300 residues and again at specific locations near residues 1800–2000 and 2400–2500. There is a highly predicted transmembrane helix between amino acid positions 44 and 69 with its transmembrane segment between residues 52 and 69.

One interesting feature of the predicted amino acid polypeptide is the sequence RRARR located at position 1069. This highly arginine rich sequence is a likely site for trypsin-like proteolytic cleavage. N-terminal amino acid sequence determinations of several of the SDS-PAGE FHA peptide bands by other workers confirms that cleavage, in fact, occurs at this location. Analysis of the resultant two parts of the FHA peptide sequence demonstrates striking differences in chemical properties: The N-terminal 98kDa fragment is highly basic with a positive hydropathy score, whereas the C– terminal 140 kDa portion is a negatively charged acidic polypeptide which has a more hydrophilic overall composition. Polypeptides of these two sizes are dominant species on FRA Western immunoblots.

Cell Recognition Site

Located at amino acid position 1097 and again at position 2599 is the tripeptide sequence RGD. This sequence is known as a "cell recognition site" for the interaction of fibronectin and other eukaryotic extracellular matrix proteins with the integrin receptor family on a variety of eukaryotic cell surfaces (Pierschbacher and Ruoslahti, Proc. Natl. Acad. Sci. USA (1984) 81:5985–5988, Ruoslahti and Pierschbacher, Science (1987) 238:491–497). Secondary structure analysis of the polypeptide sequence adjacent to these two FHA RGD sites reveals that the first of these is highly predicted to be surface exposed, hydrophilic, and antigenic. Comparison of the FHA peptide sequence adjacent to this RGD site and the sequence surrounding the RGD in fibronectin shows identity at 7 of the 9 residues. Cleavage at the RRARR processing site would leave this first RGD sequence close to the N terminius of the 214 kDa polypeptide product.

In vitro Cell Adherence

The role of several virulence factors in mediating adherence of B. pertussis to Chinese Hamster Ovary cells was evaluated. Table 3 indicates the findings:

TABLE 3

ADHERENCE OF B. pertussis STRAINS TO CHO CELLS

| Strain | Fha | Fim2 | Mean adherent bacteria per CHO cell ± SD (95% Fim3confidence interval) | % Wt |
|---|---|---|---|---|
| BP536 (vir+) | + | + | −363 ± 111 (243–483) | 100 |
| BP537 (vir−) | − | − | −2.55 ± 2.8 (0.71–4.39) | 0.7 |
| BP101 (fhaBΔ101) | − | + | −10.8 ± 5.2 (7.67–13.9) | 3.0 |
| BP-B52 (fim2B52, fim3::Km) | + | − | −317 ± 158 (146–488) | 87.3 |
| BP353 (fhaA::Tn5) | ∓ | − | −23.4 ± 13.8 (13.3–33.5) | 6.4 |
| BP-TOX6 (ptxΔ6) | + | + | −405 ± 102 (303–507) | 112 |

The results described in the above section demonstrate that the gene encoding filamentous hemagglutinin of B. pertussis and the expressed gene product are now available in intact and modified forms, for use in diagnosis, prophylaxis and therapy of pertussis. Of particular interest is the use of the gene to prepare vaccines, where the protein may be used by itself, as a fragment, as the intact expression product of the gene or the physiologically active fragment thereof, or in combination with other pertussis proteins, particularly with modified pertussis toxin, or with proteins of other pathogens. The subject gene may be used to enhance the amount of the filamentous hemagglutinin present in a live or dead B. pertussis organism or to provide for the presence of the subject proteins in other organisms, where immune response to more than one antigen is desired.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated nucleic acid comprising a first FHA nucleic acid encoding the full length 368 kDa FHA protein from Bordetella pertussis joined to a second nucleic acid sequence from other than Bordetella pertussis.

2. The isolated nucleic acid according to claim 1 wherein said first FHA nucleic acid is 10788 nucleotides in length.

3. The isolated nucleic acid according to claim 1 wherein said first FHA nucleic acid comprises nucleotides 253 through 11,040 herein.

4. An expression construct which comprises the isolated nucleic acid of any one of claims 1, 2 or 3, said isolated nucleic acid being operably linked to a third nucleic acid comprising a transcription initiation region and a fourth nucleic acid comprising a transcription termination region.

5. A prokaryotic cell transformed with the expression construct according to claim 4.

6. The cell according to claim 5 wherein said cell is a Bordetella pertussis cell.

7. A method for producing an FHA protein comprising culturing the cell of claim 5 under conditions which result in the expression of said nucleic acid of said expression construct.

8. An isolated nucleic acid comprising a first nucleic acid encoding the amino terminal 313 kDa fragment of the Bordetella pertussis FHA protein.

9. The isolated nucleic acid according to claim 8 wherein said first nucleic acid comprises nucleotides 253 through 9625 herein.

10. An expression construct with comprises the isolated nucleic acid of claims 8 or 9, said first nucleic acid being operably linked to a second nucleic acid comprising a transcription initiation region and a third nucleic acid comprising transcription termination region.

11. A prokaryotic cell transformed with the expression construct according to claim 10.

12. The cell according to claim 11 wherein said cell is a Bordetella pertussis cell.

13. A method for producing an FHA protein comprising culturing the cell of claim 11 under conditions which result in the expression of said first nucleic acid of said expression construct.

14. An isolated nucleic acid comprising a first nucleic acid encoding an amino terminal fragment of a 313 kDa FHA protein, wherein said amino terminal portion extends from the amino terminus of a 313 kDa Bordetella pertussis FHA protein and comprises at least 9 amino acids, wherein said first nucleic acid is jointed to a second nucleic acid sequence from other than Bordetella pertussis.

15. The isolated nucleic acid according to claim 14 wherein said amino terminal portion comprises at least 12 amino acid residues.

16. The isolated nucleic acid according to claim 14 wherein said isolated nucleic acid is at 100 base pairs in length.

17. The isolated nucleic acid according to claim 14 wherein said first nucleic acid comprises nucleotides 253 through 9625 herein.

18. An expression construct which comprises the isolated nucleic acid according to any one of claims 14, 15, 16 or 17, said isolated nucleic acid being operably linked to a third nucleic acid comprising a transcription initiation region and a fourth nucleic acid comprising a transcription termination region.

19. The isolated nucleic acid according to claim 1 or claim 14, wherein said second nucleic is free of the fhaA gene.

20. A prokaryotic cell transformed with the expression construct according to claim 18.

21. The cell according to claim 19 wherein said cell is a Bordetella pertussis cell.

22. A method for producing an FHA protein or peptide comprising culturing the cell of claim 19 under conditions which result in the expression of said isolated nucleic acid of said expression construct.

23. An isolated nucleic acid comprising a fragment of the nucleic acid encoding FHA protein from Bordetella pertussis having at least 100 nucleotides including nucleotides selected from the group consisting of:

(a) nucleotides encoding direct repeats located between nucleotides 1468 and 1746 herein;
(b) nucleotides encoding a motif EARKDE at nucleotide positions 3883–3900 herein, said nucleotides encoding amino acid positions 1211 to 1216 of the FHA protein;
(c) nucleotides encoding an RGD cell recognition sites at nucleotide positions 3541–3549 and 8050–8058 herein;
(d) nucleotides encoding an RRARR proteolytic site at nucleotide positions 3457–3471 herein;
(e) nucleotides encoding a motif SKQDER at nucleotide positions 9475–9492;
(f) nucleotides encoding a (PK)5 repeat which repeat begins at nucleotide position 10681 herein; and
(g) nucleotides encoding a sequence VEVVPRPKVET at nucleotide positions 10207 and 10330 herein.

24. An isolated nucleic acid comprising a fragment of the nucleic acid encoding FHA protein from *Bordetella pertussis* wherein said fragment encodes at least 12 amino acids of said FHA protein and includes nucleotides selected from the group consisting of:
(a) nucleotides encoding a motif EARKDE at nucleotide position 3883–3900 herein;
(b) nucleotides encoding an RGD cell recognition site at nucleotide positions 3541–3549 and 8050–8058 herein;
(c) nucleotides encoding an RRARR proteolytic site at nucleotide positions 3457–3471 herein; and
(d) nucleotides encoding a motif SKQDER at nucleotide positions 9475–9492.

* * * * *